United States Patent [19]
Geiger

[11] Patent Number: 5,328,575
[45] Date of Patent: Jul. 12, 1994

[54] PHOTOCHEMICAL PROCESS AND SYTEM FOR PERFORMING A PHOTOCHEMICAL PROCESS

[75] Inventor: Allen R. Geiger, Las Cruces, N. Mex.

[73] Assignee: LaSen, Inc., Las Cruces, N. Mex.

[21] Appl. No.: 926,227

[22] Filed: Aug. 6, 1992

[51] Int. Cl.$^5$ .............................. C07C 2/00; C07C 4/00
[52] U.S. Cl. ............................ 204/157.15; 204/157.6; 204/157.61; 204/157.3; 204/158.2
[58] Field of Search ................ 204/157.15, 157.61, 204/157.3, 158.2, 157.6

[56] References Cited

U.S. PATENT DOCUMENTS

| | | | |
|---|---|---|---|
| 3,274,087 | 12/1962 | Lauer | 204/157.15 |
| 3,617,936 | 11/1971 | Bjorkholm | 331/175 |
| 3,941,670 | 3/1976 | Pratt, Jr. | 204/157.61 |
| 4,045,316 | 8/1977 | Legan | 204/158 |
| 4,124,466 | 11/1978 | Morrey | 204/157.61 |

OTHER PUBLICATIONS

APS printed abstract of P.N. 3,617,936.
Haggin, J., C & E N, "Direct Conversion of Methane to Fuel, Chemicals Still Intensely Sought", pp. 33–35, Apr. 27, 1992.
Golding, Brage, "Polymers and Resins, Their Chemistry and Chemical Engineering", D. Van Nostrand Company, Inc., 1959, pp. 36–41.
Fox, Joseph M., et al., "Direct Methane Conversion Process Evaluations", Bechtel National Inc., San Francisco, Calif., AICHE 1989 spring national meeting, Apr. 2–6, 1989, pp. 1–25.

Primary Examiner—John Niebling
Assistant Examiner—C. Delacroix-Muirheid
Attorney, Agent, or Firm—Kramer, Brufsky & Cifelli

[57] ABSTRACT

An apparatus and method photochemically converts a first hydrocarbon into at least one other hydrocarbon, such as the conversion of methane to ethane and other higher hydrocarbons. The first hydrocarbon is injected through a high-temperature nozzle into a first reaction chamber surrounded by a first array of optical parametric oscillator/lasers (OPOLs). The secondary radiation of the OPOLs is directed into the first reaction chamber and dissociates the first hydrocarbon into the at least one other hydrocarbon. For the conversion of methane to ethane, the secondary radiation of the OPOLs is preferably within the region of approximately 3.0 microns. In a recirculating stage, residual first hydrocarbon released from the first reaction chamber is circulated through a second reaction chamber surrounded by a second array of optical parametric oscillator/lasers (OPOLs) to further dissociate the residual second hydrocarbon into the at least one other hydrocarbon. The higher hydrocarbons, such as ethane, are removed and collected by distillers after being released from each reaction chamber.

20 Claims, 3 Drawing Sheets

PHOTOCHEMICAL PROCESS AND SYTEM FOR PERFORMING A PHOTOCHEMICAL PROCESS

FIELD OF THE INVENTION

The present invention relates to chemical processes and, more particularly, to photocatalytic or photochemical processes and apparatus for performing such processes.

BACKGROUND INFORMATION

Methane is a relatively plentiful natural resource. Methane rich gas is formed as a byproduct during coal gasification and Fischer-Tropsch synthesis, and methane is also the primary constituent of both natural gas and the associated gas resulting from crude oil production. These gases have little value, however, unless they can be converted into a transportable form or converted into other more commercially desirable and transportable chemicals. In many places in the world, abundant natural gas is being flared because it is too costly to transport to the site of conversion or utilization as a fuel. This is a significant waste by any standard. The direct conversion of methane to liquid fuels and chemicals of commercial importance has been an intensely sought after goal.

A principal theme of current work on direct conversion is catalytic conversion. Haggin, J., *C & E N*, "Direct Conversion of Methane to Fuel, Chemicals Still Intensely Sought", pp. 33–35, Apr. 27, 1992. The various reported methods of catalytic conversion use sulfide molybdenum catalysts, and metal oxide catalysts, for example. So far, the known methods of catalytic conversion have been too inefficient to attract significant commercial investment.

It is an object of the present invention to overcome the drawbacks and disadvantages of known methods of converting methane to ethane and other higher hydrocarbons, and similar methods of conversion.

SUMMARY OF THE INVENTION

The present invention is directed to an apparatus for performing a photochemical reaction, comprising a reaction chamber for receiving a first molecular substance for photochemical conversion of the first molecular substance into at least two second molecular substances. At least one optical parametric oscillator of the apparatus generates secondary radiation from primary radiation by parametric interaction of the primary radiation with an optically nonlinear medium, and at least a portion of the secondary radiation is directed into the reaction chamber to dissociate the first molecular substance into the at least two second molecular substances.

In one embodiment of the present invention, the at least one optical parametric oscillator is an optical parametric oscillator/laser (OPOL). The OPOL includes an optical pump source for generating pump radiation, and an OPOL material responsive to the pump radiation to generate laser radiation, and responsive to the laser radiation to generate parametric optical radiation. The apparatus preferably includes an array of OPOLs surrounding at least a portion of the reaction chamber for directing at least a portion of the secondary radiation generated by the array into the reaction chamber.

One embodiment of the present invention comprises a first stage and a second stage coupled to the first stage. The first stage includes a first reaction chamber and a first optical parametric oscillator for directing secondary radiation into the first reaction chamber to dissociate the first molecular substance into at least two second molecular substances. The second stage includes a second reaction chamber for receiving any residual first molecular substance from the first stage, and a second optical parametric oscillator for directing secondary radiation into the second reaction chamber to dissociate the residual first molecular substance into the at least two second molecular substances.

This apparatus of the present invention may further comprise a first distiller located downstream relative to the first reaction chamber for removing and collecting at least a portion of at least one second molecular substance from the first reaction chamber. A second distiller is preferably located downstream relative to the second reaction chamber for removing and collecting at least a portion of at least one second molecular substance from the second reaction chamber. One embodiment of the present invention also comprises a first heat exchanger for cooling the first optical parametric oscillator, and a second heat exchanger for cooling the second optical parametric oscillator.

The present invention is also directed to a method for performing a photochemical reaction comprising the steps of introducing a first molecular substance into a chamber; and generating secondary radiation with at least one optical parametric oscillator, and directing at least a portion of the secondary radiation into the chamber to promote the reactivity of the first molecular substance. In one embodiment of the present invention, the first molecular substance is dissociated into at least two second molecular substances.

In one embodiment of the present invention, the first molecular substance is a hydrocarbon which is dissociated into at least one second hydrocarbon. The first hydrocarbon can be methane and the at least one second hydrocarbon can be ethane, for example.

One embodiment of the present invention further comprises the steps of directing residual first molecular substance released from the chamber into a second chamber; generating secondary radiation with a second optical parametric oscillator; and directing at least a portion of the secondary radiation into the second chamber to dissociate the residual first molecular substance into at least two second molecular substances. One embodiment of the present invention further comprises the steps of removing and collecting at least a portion of at least one second molecular substance from each chamber by distilling the second molecular substance. One embodiment of the present invention also comprises the step of recirculating residual first molecular substance released from the second chamber back through the second chamber to dissociate the residual first molecular substance into at least two second molecular substances.

One advantage of the apparatus and method of the present invention is that because they employ at least one optical parametric oscillator, and preferably at least one optical parametric oscillator/laser (OPOL), relatively inexpensive photons can be generated to perform chemical reactions which have until now been achieved only by catalytic processes and/or have been thermally driven. As will be recognized by those skilled in the art, the apparatus and method of the present invention are particularly useful for carrying out reactions that to date have been thermodynamically inefficient.

Other advantages of the apparatus and method of the present invention will become apparent in view of the following detailed description and accompanying drawings.

DETAILED DESCRIPTION

Figure 1:
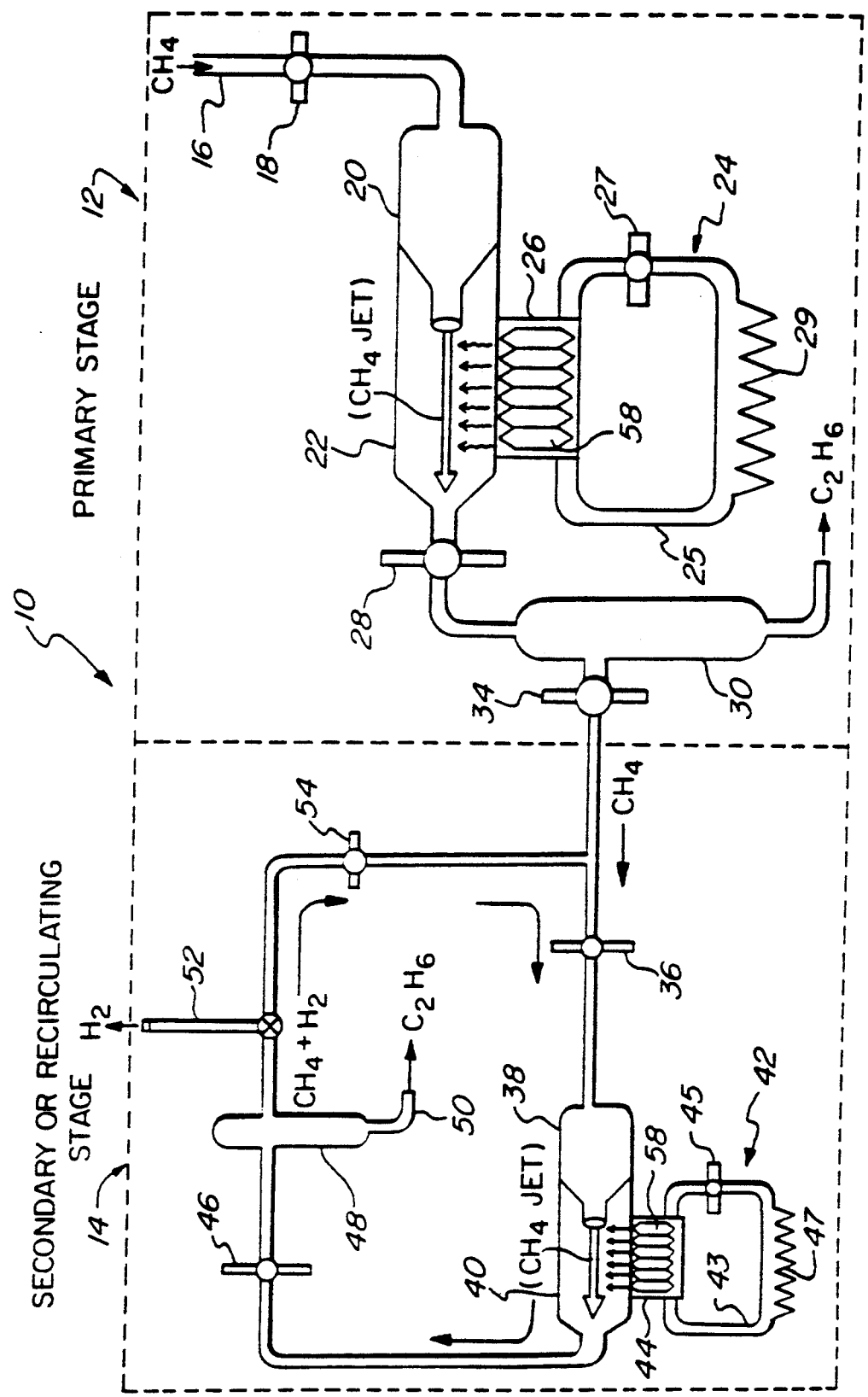
FIG. 1 is a schematic illustration of a system embodying the present invention for performing a photocatalytic process of the present invention.

In FIG. 1, a system embodying the present invention for performing a photochemical process of the present invention is indicated generally by the reference numeral 10. The system 10 includes a primary stage 12 and a secondary or recirculating stage 14. In the embodiment of the present invention illustrated, the system 10 is used for the photochemical conversion of methane ($CH_4$) to ethane ($C_2H_6$) and other higher hydrocarbons. As will be recognized by those skilled in the art, however, the system and process of the present invention can equally be used to carry out a wide variety of other photocatalytic or photochemical reactions. These may include, for example, the manufacture of various other higher hydrocarbons from lower hydrocarbons, various biological and pharmaceutical chemicals, and various bond arrangements and photo-activated drugs.

In the primary stage 12, the methane ($CH_4$) flows into the system 10 through a conduit 16 and is compressed by a compressor 18. The compressed methane ($CH_4$) is then heated and injected through a high-temperature nozzle 20 into a reaction chamber 22. An optical parametric oscillator/laser system (OPOL system) 24, which includes an array of optical parametric oscillator/lasers (OPOLs) 26 coupled to one another, is located adjacent to the reaction chamber 22 so that the array of OPOLs 26 are arranged around the reaction chamber. Thus, the methane ($CH_4$) injected into the reaction chamber 22 is subject to radiation from the array of OPOLs 26. The OPOL array 26 is preferably arranged around the reaction chamber 22 in order to achieve the highest flux densities possible.

The wavelength of the radiation of the OPOL array 26 is selected based upon the absorption spectra of the molecule to be broken down. In the case of methane ($CH_4$), the region of approximately 3.313 microns can provide multi-photon absorptions breaking the methane molecules ($CH_4$) into ($CH^-_3 + H^+$). These ions react with each other to form the higher hydrocarbon ethane ($C_2H_6$) plus hydrogen ($H_2$). Another option is to operate the OPOLs 26 in the near infrared region (approximately 1.5 microns) for photo-dissociating the methane ($CH_3^- + H^+$ or $CH_2^{--} + H_2$) to ethane and/or unsaturated hydrocarbons plus hydrogen. One advantage of employing the OPOL array 26 is that it can be precisely tuned to emit the two wavelengths of interest (3.313 and 1.5 microns), and thus can efficiently supply the energy necessary for dissociation.

As shown in FIG. 1, the OPOL system 24 includes a conduit 25 for carrying a cooling fluid, which is circulated by a pump 27 through the OPOL array 26 and a heat exchanger 29 in order to cool the array. Once the methane flow passes through the OPOL radiation field in the reaction chamber 22, it is pumped by a pump 28 into a distiller 30 where it is expansion cooled. The heavier ethane ($C_2H_6$) is liquified in the distiller 30 and is removed through an outlet conduit 32. The residual methane ($CH_4$) and hydrogen ($H_2$) are injected by a pump 34 into the second stage 14 in order to photodissociate the remaining methane. The secondary stage 14 operates in essentially the same way as the primary stage 12, except that the residual methane ($CH_4$) and hydrogen ($H_2$) are recirculated through the system until substantially all of the methane is converted and the hydrogen is removed.

The secondary stage 14 includes a compressor 36 for compressing the methane ($CH_4$), and a high-temperature nozzle 38 for heating and injecting the compressed methane into a reaction chamber 40. Another OPOL system 42 including an array of OPOLs 44 is located adjacent to the reaction chamber 40 for producing a radiation field within the reaction chamber in order to break down the residual methane into ($CH^-_3 + H^+$), and form the higher hydrocarbon ethane ($C_2H_6$) plus hydrogen ($H_2$). The OPOL system 42 includes a conduit 43 for carrying a cooling fluid, which is circulated by a pump 45 through the OPOL array 44 and a heat exchanger 47 to cool the array.

The residual methane ($CH_4$), ethane ($C_2H_6$), and hydrogen ($H_2$) are then pumped by a pump 46 into a distiller 48 where they are expansion cooled. The heavier ethane ($C_2H_6$) is liquified in the distiller 48 and is removed through an outlet conduit 50. The molecular hydrogen ($H_2$) is removed through an outlet conduit 52 by any of various catalytic processes known to those skilled in the art. Any residual methane ($CH_4$) and hydrogen ($H_2$) is then recirculated back through the second stage 14 by a pump 54 until substantially all of the methane is converted and the hydrogen is removed. The molecular hydrogen ($H_2$) can either be collected or burned in order to provide heat and/or power for the OPOL arrays 26 and 44 in a manner known to those skilled in the art.

Figure 2:
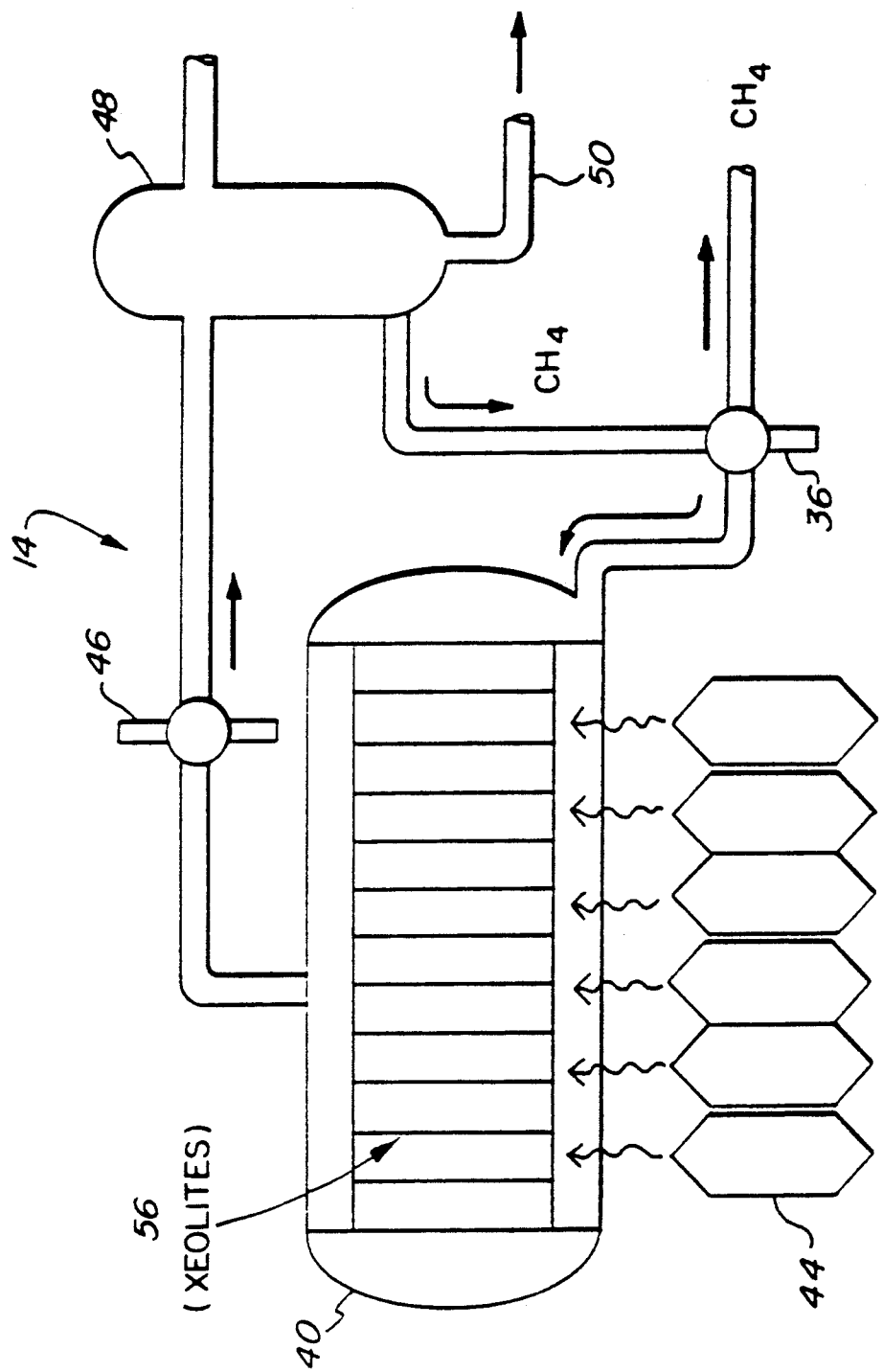
FIG. 2 is a schematic illustration of the secondary stage of the system of FIG. 1 illustrating the reaction chamber in further detail.

As illustrated typically by the reaction chamber 40 in FIG. 2, the reaction chambers 22 and 40 preferably include zeolites 56 to control the polymerization of the photochemically activated materials.

Figure 3:
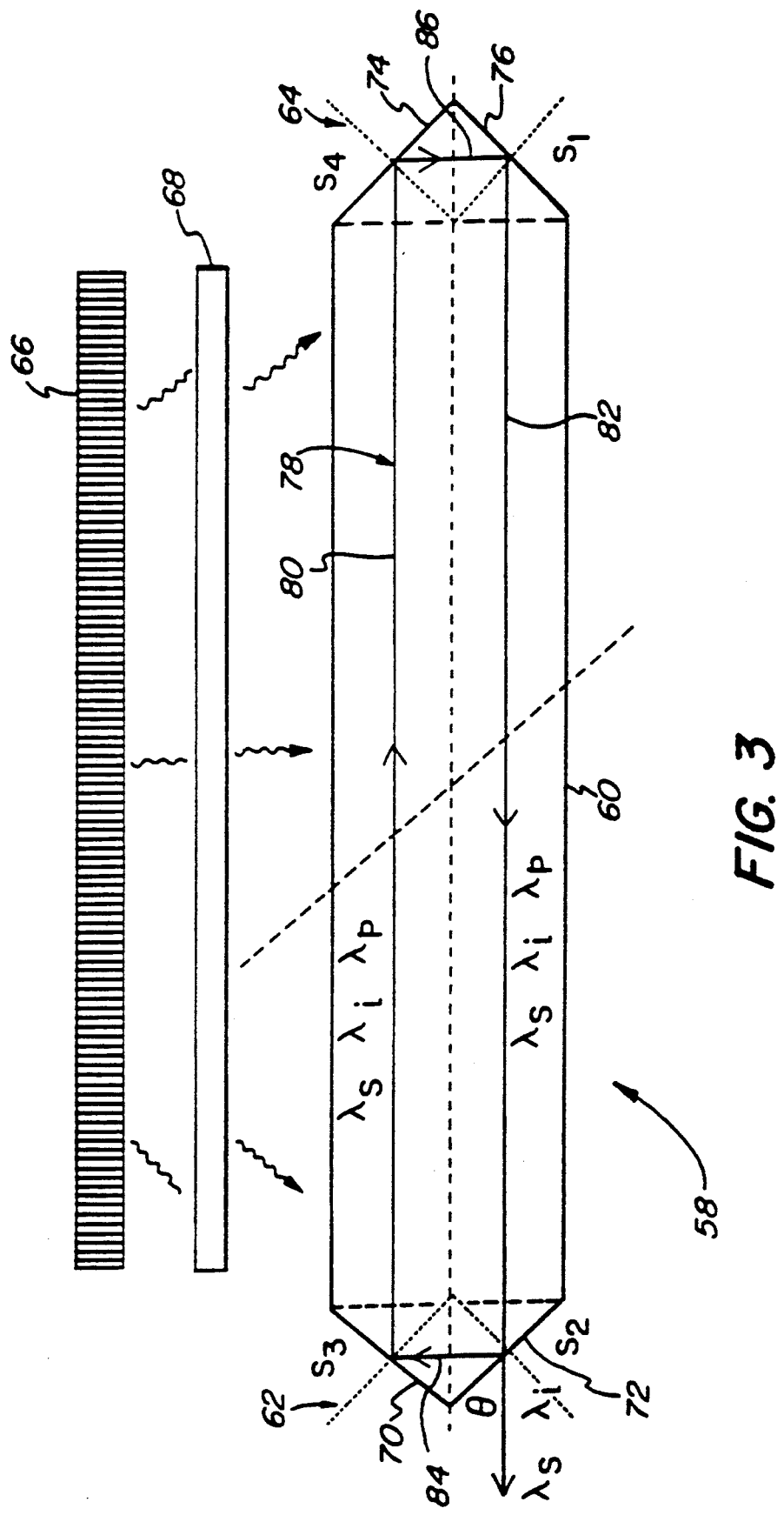
FIG. 3 is a schematic illustration of a typical OPOL of the OPOL arrays of the system of FIG. 1.

As shown in FIG. 1, each of the OPOL arrays includes six OPOLs 58 coupled to each other. This number is only exemplary, however, and can be changed as desired depending upon the particular application of the system of the present invention. In FIG. 3, a typical OPOL from the OPOL array 26 is illustrated and indicated generally by the reference numeral 58. Because in the embodiment of the present invention illustrated each of the OPOLs in the OPOL arrays 26 and 42 are identical, only a single typical OPOL 58 is described and illustrated in FIG. 3. Each OPOL 58 can be substantially the same as any of the OPOLs shown and described in co-pending patent application Ser. No. 07/777,705, filed Oct. 15, 1991, entitled "An Internally Stimulated Optical Parametric Oscillator/Laser", now U.S. Pat. No. 5,195,104 which is assigned to the same assignee as the present invention, and is hereby expressly incorporated by reference as part of the present disclosure.

Each OPOL 58 is constructed to generate secondary (parametrically generated) radiation from monochromatic coherent primary radiation by means of parametric interaction of the primary radiation with an optically nonlinear medium. The primary radiation has a known frequency and it propagates through the nonlinear medium and is converted into secondary radiation at two lower frequencies (longer wavelengths). The secondary or parametric radiation has two components, typically referred to as a signal wavelength and an idler wavelength.

The typical OPOL 58 illustrated in FIG. 3 includes an OPOL rod 60, which comprises a material capable of optical parametric oscillation and lasing transitions as described in the above-referenced patent application. An end cap 62 is disposed at one end of the OPOL rod 60, and an end cap 64 is disposed at the other end of the OPOL rod 60. The end caps 62 and 64 can be separate elements or can be integrally formed as a part of the OPOL rod 60. An optical pump source 66 provides pump radiation to the OPOL rod 60. The pump radiation is focused on the OPOL rod 60 by a cylindrical lens 68.

The end cap 62 includes surfaces 70 and 72 which internally reflect laser radiation and optical parametric radiation generated within the OPOL rod 60. The other end cap 64 includes surfaces 74 and 76 which internally reflect laser radiation and optical parametric radiation. The surfaces 70, 72, 74 and 76 may have coatings to insure that the desired reflection occurs. The surfaces 70, 72, 74 and 76 are each oriented at an angle, such as 45° or the Brewster angle, with respect to the optical axis of the OPOL rod 60 so as to reflect radiation in a closed loop within the OPOL rod 60. The coatings on the surfaces 70, 72, 74 and 76 are selected to reflect the laser radiation and the optical parametric radiation generated within the OPOL rod 60, except that one of the surfaces, such as the surface 72, designated as an output of the OPOL system is partially reflective at the desired output wavelength. Laser radiation and optical parametric radiation generated within the OPOL rod 60 are reflected by surfaces 70, 72, 74 and 76 to form a closed loop path, or ring 78 within the OPOL rod 60. The closed loop path 78 traversed by the laser photons and the OPOL photons includes sections 80 and 82 along the length of the OPOL rod and sections 84 and 86 within the end caps 62 and 64, respectively. The sections 84 and 86 are perpendicular to the sections 80 and 82. The sections 80 and 82 are parallel to a selected nonlinear axis of the OPOL material so that generation of laser photons and optical parametric oscillation takes place along these sections.

The pump source 66 stimulates generation of laser photons within the OPOL rod 60. The laser photons circulate in a ring along the path 78 defined by sections 80, 82, 84 and 86. When the laser photons reach the parametric oscillation threshold, OPO photons at signal and idler wavelengths are generated. The OPOL photons also circulate around the closed loop path 78 within the OPOL rod 60 and end caps 62, 64. One of the surfaces 70, 72, 74 or 76 can be coated to act as an output coupler for the wavelength of interest. Because the OPOL system shown in FIG. 3 is resonating at the laser wavelength, the signal wavelength and the idler wavelength, the OPOL is said to be triply resonant.

One advantage of the OPOL 58 of FIG. 3 is that it is self-walkoff compensating. As the photons circulate, the ring is symmetric with respect to the refractive optical axis. As the laser and parametric photons traverse one section of the ring, they "walk" away from each other and on the other section, they merge.

One advantage of employing the OPOLs 58 is that they provide economic photons nearly anywhere in the region from the ultraviolet to the mid-infrared. A single OPOL array can provide a multitude of wavelengths, thus providing the cost of scale for the system. The OPOL 58 also has an adjustable bandwidth feature and can be designed to emit multiple wavelengths, as described in the above-referenced patent application. These features can be used to facilitate precise manipulation and control of photocatalytic or photochemical processes, as described above. Thus, the OPOLs 58 can generate relatively inexpensive photons for reactions that have until now only been achieved by catalytic processes and/or have been thermally driven, such as the conversion of methane ($CH_4$) to ethane ($C_2H_6$) and other higher hydrocarbons described above.

It should be pointed out, however, that standard optical parametric oscillators (OPOs), particularly those pumped within a laser cavity, or other suitable radiation source, could be used in the system of the present invention instead of the OPOLs illustrated in FIG. 1. However, as will be recognized by those skilled in the art, one advantage of the OPOLs is that they can be precisely tuned to the absorption band of the molecules of interest, and operate efficiently at that wavelength.

In another embodiment of the present invention, rather than converting the methane into the higher hydrocarbons by using the OPOLs 24 and 42 at 3,313 microns, the methane molecular overtone at 1.665 microns is used instead. One advantage of this embodiment is that either an OPO or an OPOL pumped near the infrared is significantly more efficient at producing energy at its signal wavelengths. Another advantage is that at this wavelength (approximately 1.665 microns), only 2 or 3 photons are required to reach the quasi-continuum molecular state, and only 6 photons are required for dissociation, as compared to 12 photons at 3.313 microns. By using 1,665 microns and/or 3.313 microns it is also possible to remove two hydrogens from the methane forming the carbine ($CH_2--$) radical. This requires only the addition of one 3.313 micron photon. The carbine radical is extremely reactive and will tend to form multiple-bond carbon compounds (unsaturated hydrocarbons). Thus, in the methane reaction there are two possible pathways:

(1) $CH_4 \xrightarrow{106 \text{ kcal/mole}} CH_3^- + H^+$, which tends to yield saturated hydrocarbons; and (2) $CH_4 \xrightarrow{112 \text{ kcal/mole}} CH_2-- + H_2$, which tends to yield unsaturated hydrocarbons.

As will be recognized by those skilled in the art, a significant advantage of the present invention is that because either an OPO or OPOL can produce economical photons over a wide spectral range, the system of the present invention can be used for carrying out a wide variety of photocatalytic or photochemical reactions. Yet another advantage of the apparatus and method of the present invention is that they can be used to efficiently carry out reactions that had previously been considered thermodynamically inefficient. As will be recognized by those skilled in the art, the present invention will have wide applications beyond the methane conversion described above, because the OPOLs 26 (or other suitable radiation source) can selectively enhance a kinetic reaction without requiring the addition of heat to the material of interest. This increase in kinetic reaction may be used for dissociation as described above, or for the activation of a particular chemical or catalyst.

The method and apparatus of the present invention employs abundant, inexpensive infrared photons to promote chemical reactivity, and in turn carry out chemical processing with higher efficiencies and higher rates than have been achieved to date. The infrared radiation generated by the OPOLs 26 (or other suitable radiation source) can be used to control the shape of the potential energy surface on which the chemical reaction occurs. Many reaction rates can therefore be accelerated, and these rates may allow reaction channels to be created, leading to new reaction products.

In general, even for a thermodynamically favored reaction to proceed, a significant fraction of the reactant species must have enough energy to overcome the energy (or activation) barriers. In other words, the random collisions between the reactants, or the internal motions of a dissociating molecule, must be violent enough to give the vibrational motion along the reaction coordinates sufficient energy to overcome any energy barriers along the reaction path. In the prior art, there have been two well-known approaches to facilitating reactions. One is to lower the energy barriers with a catalyst. The other is to heat the reactants in order to give the reactant collisions or internal molecular motions sufficient energy to overcome the energy barriers. As will be recognized by those skilled in the art, the apparatus and method of the present invention can be employed to enhance both of these methods of facilitating reactions.

In a unimolecular dissociation, for example, the molecular vibrations must boost the internal energy of the molecule to the point that the vibrations along the reaction coordinates exceed the maximum energy separating reactants and products. The reaction rate is proportional to the number of molecules having the requisite energy to dissociate. If the energy promotion is achieved thermally, then the reaction system will tend to be in equilibrium with a thermal radiation field whose energy (wavelength) distribution follows the black body curve. As an example, if the reaction system involves the following dissociations:

$$CH_4 \rightarrow CH_3^+ + H^+$$

$$H_2O \rightarrow HO^+ + H^+$$

then the reaction coordinates are essentially the stretch of the CH and OH bonds. These bonds have a resonant wavelength of about 3.0 microns, and the black body distribution has a maximum near 3.0 microns at a temperature of approximately 1000° K. This is close to the temperature used to run a typical synthesis gas reaction, such as:

$$CH_4 + H_2O \rightarrow CO + 3H_2$$

Thus, in such prior thermally-driven reactions, a relatively large amount of thermal energy is required to drive the reaction.

In the apparatus and method of the present invention, on the other hand, intense, abundant, monochromatic infrared radiation is used to alter the vibrational distribution away from the black body shape by employing the OPOLs 26 (or other suitable radiation source). The radiation directly promotes vibrations that resonate near the wavelength of the radiation, and thus alters the black body distribution of the molecules of interest into a closely-grouped shape forming a peak at the selected wavelength. For example, approximately 3.0 micron infrared radiation upwardly promotes the molecules in the system by a sequence of vibrational states. The molecules absorb the radiation, and this energy is in turn transformed into vibrational energy, significantly enhancing the reactivity of the molecules of interest. Application of infrared radiation in accordance with the present invention effectively raises the temperature of the system in comparison to prior systems which require the input of heat, without the need for such thermal energy. For example, reactivities which were thermally achievable at approximately 2000° K may be reached at approximately 300° K–400° K with the apparatus and method of the present invention. The present invention may therefore also be employed to drive reactions that have otherwise been thermodynamically unfavorable.

As will be recognized by those skilled in the art, the method and apparatus of the present invention can also be used to fine tune the thermal promotion of reactants by selecting the appropriate wavelength of the radiation in order to increase the vibrational states of the reactants of interest. The present invention can similarly be incorporated within known catalytic reactions by enhancing the vibrational states of the molecules of interest, to in turn promote the catalytic reaction.

As can be seen, the infrared promotions of the present invention impart vibrational energy to the reactant molecules. In doing so, the infrared radiation creates anomalous vibrational populations, effectively altering the ground state, electronic energy potential surfaces of the molecules. In some circumstances, this alteration can actually give the reacting system access to reaction channels or reaction paths that have otherwise been unreachable.

I claim:

1. A method for performing a photochemical reaction comprising the following steps:
   introducing a first molecular substance into a chamber;
   tuning the outlet of at least one optical parametric oscillator/laser to at least one absorption band of the first molecular substance; and
   directing the at least one portion of the output of the optical parametric oscillator laser tuned to the absorption band of the first molecular substance into the chamber to dissociate the first molecular substance.

2. A method as defined in claim 1 wherein the first molecular substance is dissociated into at least two second molecular substances.

3. A method as defined in claim 2, wherein the first molecular substance is a hydrocarbon which is dissociated into at least one second hydrocarbon.

4. A method as defined in claim 3, wherein the first hydrocarbon is methane and the at least one second hydrocarbon is ethane.

5. A method as defined in claim 2, further comprising the step of removing and collecting at least a portion of at least one second molecular substance by distilling the at least one second molecular substance.

6. A method as defined in claim 2, further comprising the steps of directing a residual first molecular substance released from the chamber into a second chamber, and directing at least a portion of the output of at least one optical parametric oscillator/laser tuned to the absorption band of the first molecular substance into the second chamber to dissociate the residual molecular substance into at least two second molecular substances.

7. A method as defined in claim 6, further comprising the steps of removing and collecting at least a portion of at least one second molecular substance from each chamber by distilling the at least one second molecular substance.

8. A method as defined in claim 6, further comprising the step of recirculating residual first molecular substance released from the second chamber back through the second chamber to dissociate the residual first molecular substance into at least two second molecular substances.

9. A method as defined in claim 4, wherein the wavelength of the output of the at least one optical parametric oscillator is within the region of approximately 3.0 microns.

10. A method as defined in claim 1, wherein the step of tuning the output of the optical parametric oscillator/laser includes an optical pump source for generating pump radiation, and an OPOL material responsive to the pump radiation to generate laser radiation and responsive to the laser radiation to generate parametric optical radiation.

11. A method as defined in claim 1, further comprising the step of compressing the first molecular substance prior to introduction into the chamber.

12. A method as defined in claim 1, further comprising the step of heating the first molecular substance prior to introduction into the chamber.

13. A method of performing a photochemical reaction comprising the following steps:
    introducing a first molecular substance into a chamber;
    tuning the output of at least one optical parametric oscillator/laser to at least one predetermined wavelength corresponding to at least one absorption band of the first molecular substance; and
    altering the vibrational distribution of the at least one optical parametric oscillator into the first molecular substance and promoting molecular vibration approximately at the predetermined wavelength to from a peak within the vibrational distribution of the first molecular substance at approximately the predetermined wavelength and dissociate the first molecular substance.

14. A method as defined in claim 13, wherein the first molecular substance is methane which is dissociated into at least one second molecular substance including ethane.

15. A method as defined in claim 14, wherein the at least one predetermined wavelength is selected from the group including approximately 3.313 microns and approximately 1.665 microns.

16. A method as defined in claim 13, further comprising the step of compressing the first molecular substance prior to introduction into the chamber.

17. A method as defined in claim 13, further comprising the steps of directing residual first molecular substance released from the chamber into a second chamber, and altering the vibrational distribution of the first molecular substance within the second chamber by directing the output of at least one optical parametric oscillator/laser tuned to at least one wavelength corresponding to at least one absorption band of the first molecular substance and promoting molecular vibration approximately at the at least one wavelength to form a peak within the vibrational distribution at the wavelength and dissociate the first molecular substance.

18. A method for performing a photochemical reaction, comprising the following steps:
    tuning the output of at least one optical parametric oscillator/laser to at least one absorption band of a molecular substance; and
    directing the output of the at least one optical parametric oscillator/laser into the molecular substance and dissociating the molecular substance.

19. A method as defined in claim 18, further comprising the steps of tuning the output of the at least one optical parametric oscillator/laser to both a primary absorption band and a molecular overtone of the molecular substance, and directing the output of the at least one optical parametric oscillator/laser into the molecular substance and dissociating the molecular substance.

20. A method as defined in claim 19, wherein the molecular substance is methane, and the output of the at least one optical parametric oscillator/laser is tuned to a primary absorption band of approximately 3.313 microns and a molecular overtone of approximately 1.665 microns.

* * * * *